United States Patent [19]

Stahl et al.

[11] Patent Number: 5,702,724
[45] Date of Patent: Dec. 30, 1997

[54] PROCESS FOR THE PREPARATION OF AN ORAL SOLID DOSAGE FORM CONTAINING DICLOFENAC

[75] Inventors: Peter Heinrich Stahl, Freiburg, Germany; Claudio Gamboni, Allschwil, Switzerland

[73] Assignee: Ciba-Geigy Corporation, Summit, N.J.

[21] Appl. No.: 556,979

[22] PCT Filed: May 24, 1994

[86] PCT No.: PCT/EP94/01662

§ 371 Date: Dec. 6, 1995

§ 102(e) Date: Dec. 6, 1995

[87] PCT Pub. No.: WO94/28936

PCT Pub. Date: Dec. 22, 1994

[30] Foreign Application Priority Data

Jun. 8, 1993 [CH] Switzerland ............... 1711/93

[51] Int. Cl.$^6$ ............... A61K 9/28; A61K 9/36
[52] U.S. Cl. ............... 424/465; 424/474; 424/479
[58] Field of Search ............... 424/464, 465, 424/474, 479

[56] References Cited

U.S. PATENT DOCUMENTS 5,231,089  7/1993  Bodor ............... 514/58

FOREIGN PATENT DOCUMENTS

| 0487774 | 6/1992 | European Pat. Off. |
| 59-059632 | 4/1984 | Japan. |
| 59-084821 | 5/1984 | Japan. |
| 9200725 | 1/1992 | WIPO. |

OTHER PUBLICATIONS

Derwent Publications Ltd., AN 84–123447, Apr. 1984.
Derwent Publications Ltd., AN 84–161005, May 1984.

*Primary Examiner*—Thurman K. Page
*Assistant Examiner*—James M. Spear
*Attorney, Agent, or Firm*—Marla J. Mathias; Gregory D. Ferraro

[57] ABSTRACT

The invention relates to a novel advantageous process for the preparation of an oral solid dosage form containing diclofenac or a pharmaceutically acceptable salt thereof. The dosage form is obtainable by direct compression of an inclusion compound consisting of diclofenac, or a salt thereof, with γ-cyclodextrin. The inclusion compound itself is novel and is likewise an object of the invention.

5 Claims, No Drawings

PROCESS FOR THE PREPARATION OF AN ORAL SOLID DOSAGE FORM CONTAINING DICLOFENAC

This is a 371 of International Application PCT/EP94/01662, filed May 24, 1994.

The present invention relates to a novel advantageous process for the preparation of an oral solid dosage form containing diclofenac or a pharmaceutically acceptable salt thereof, to the inclusion compound of diclofenac or a pharmaceutically acceptable salt thereof with γ-cyclodextrin, useful as intermediate for said process, as well as to a process for the preparation of said inclusion compound.

A variety of therapeutic agents of different structure, especially non-steroidal antiflammatory drugs (NSAID), is available for the treatment of painful inflammatory diseases, e.g. rheumatism.

Numbered among this group of NSAIDs of first choice is the sodium salt of diclofenac, which has long been introduced in numerous countries under the registered trademark Voltaten® (Ciba-Geigy) and which is available in different dosage forms such as dragées, suppositories or injection solutions.

Quite generally, the oral administration of this therapeutic agent in solid dosage forms such as tablets or dragées affords advantages over other, for example parenteral, dosage forms. Diseases that have to be treated by administering injections are felt purely subjectively to be more serious than other diseases in the treatment of which the administration of tablets or dragées is little noticed. The suitability of such dosage forms for self-medication by patients themselves is especially advantageous, whereas parenteral dosage forms, aside from a few exceptions, have to be administered by the physician or authorised auxiliary medical personnel.

With the exception of less directly compressable therapeutic agents such as acetylsalicylic acid, phenobarbitone, phenacetin, coffein, ascorbic acid, ammonium chloride or potassium chloride, tablets or dragées are prepared in multistep processes in which granulates are formed as intermediates. Granulates can be produced by different methods, typically by moist granulation or compacting. The granulates are subsequently compressed to tablets that may be coated in a further step to film-coated tablets or sugar-coated dragées. The technical literature takes the unequivocal view that the direct compression of therapeutic agents without granulate formation has advantages over the compression of granulates, which have to be prepared in a first step with an additional process step. So far it is not known of diclofenac or a salt thereof that this important therapeutic drug can be compressed direct to break-resistant tablets.

A further advantage of tablets and dragées obtained by direct compression results from the increased concentration of the therapeutic agent, which can usually be raised to over 50% by weight. Usually, therefore, smaller amounts of excipients are required for direct compression than for the compression of granulates. Given a predetermined tablet size, therefore, it is possible to increase the concentration of therapeutic agent or, given a predetermined dose, to reduce the size of the tablet.

Hence it is the object of this invention to prepare solid oral dosage forms such as tablets or dragées containing the therapeutic drug diclofenac, or a pharmaceutically acceptable salt thereof, by direct compression. This object is achieved by utilisation of the surprising discovery that the therapeutic drug diclofenac, or a salt thereof, with γ-cyclodextrin forms a defined inclusion compound that can be compressed direct to tablets or dragées.

Accordingly, the invention relates to a process for the preparation of a compressed dosage form for the therapeutic drug diclofenac or a pharmaceutically acceptable salt thereof, which comprises preparing an inclusion compound consisting of diclofenac, or a pharmaceutically acceptable salt thereof, and γ-cyclodextrin, and compressing said inclusion compound directly, with the addition of optional excipients conventionally employed in the preparation of solid dosage forms, and, if desired, further processing the compressed tablet core so obtained to another solid dosage form.

A further object of the invention is the inclusion compound as defined herein formed from diclofenac, or a pharmaceutically acceptable salt thereof, and γ-cyclodextrin, which can be used as intermediate in the process for the preparation of a directly compressed dosage form. The characterisable inclusion compound formed from diclofenac sodium salt and γ-cyclodextrin is especially preferred.

A further object of the invention is the process for the preparation of said inclusion compound.

The terms used throughout this specification are defined as follows within the scope of the description of the present invention:

The term "compressed dosage form" embraces tablets or dragées that disintegrate in the stomach or in the interconnecting part of the gastrointestinal tract (duodenum) and which are able to release the therapeutic drug diclofenac or a pharmaceutically acceptable salt thereof, with or without controlled release of the active drug.

Tablets or dragées (without control of drug release) are single-dose, solid dosage forms for peroral administration that can be prepared by direct compression of the inclusion compound formed from diclofenac, or a pharmaceutically acceptable salt thereof, and γ-cyclodextrin, with or without the addition of suitable excipients, by means of standard tabletting methods. Dragées are distinguished from tablets by providing them with an additional coating, typically a sugar, shellac, coloured or film coating.

Compressed dosage forms with controlled release of therapeutic drug are distinguished by accelerated or delayed, as well as quantitatively controlled, release of drug. Thus tablets with accelerated release of therapeutic drug are formed with disintegrants such as crosslinked polyvinyl pyrrolidone (Polyplasdone®XL or Kollidon® CL) or reactive excipients (effervescent mixtures) that effect rapid disintegration of the tablet in the presence of water, for example so-called effervescent tablets that contain an acid in solid form, typically citric acid, which acts in water on a base containing chemically combined carbon dioxide, for example sodium hydrogen carbonate or sodium carbonate, and releases carbon dioxide.

Compressed dosage forms with delayed release and, preferably, quantitatively controlled release, of the therapeutic drug are defined in the technical literature by different terms such as enteric-coated tablets, tablets with modified drug release, release systems or oral therapeutic systems. These definitions meet a therapeutically determined objective, typically the delayed release of a drug to effect a reduction of local overconcentrations because of the risk of irritation to gastric or intestinal niucosa (ulcer problems), reduction of the release of a loading dose administered in initial overconcentration, or prolonged release. A wide range of dosage forms are known whose properties are defined by terms such as sustained release, controlled release, prolonged release, repeat or repeated release or delayed release. The preferred dosage forms are controlled release or sustained release forms that not only delay release of the active drug over a period of time but also release it in a controlled amount. Such dosage forms are known as oral osmotic systems (OROS), coated tablets, matrix tablets, film-coated tablets, press-coated tablets, multilayer tablets and the like.

A pharmaceutically acceptable salt of diclofenac, o-(2, 6-dichlorophenylamino)phenylacetic acid, q.v. Merck Index, Eleventh Edition No. 3071, is preferably the sodium or potassium salt, and also the salt with an amine, e.g. a mono-, di- or tri-$C_1$–$C_4$alkylamine, e.g. ethanolamine, e.g. diethylamine or triethylamine, hydroxy-$C_2$–$C_4$alkylamine, e.g. ethanolamine, hydroxy-$C_2$–$C_4$alkyl-$C_1$–$C_4$alkylamine, e.g. dimethylethanolamine, or a quaternary ammonium salt, e.g. the tetramethylammonium salt or the choline salt of diclofenac.

The respective inclusion compound consisting of diclofenac, or a pharmaceutically acceptable salt thereof, and γ-cyclodextrin is novel and is an object of the invention. The following characteristic data are given for the inclusion compound of diclofenac sodium salt with γ-cyclodextrin, hereinafter referred to as γ-cyclodextrin·diclofenac sodium:

1. Elemental analysis (based on the anhydrous sample):

| Element | theory | found |
|---|---|---|
| γ-cyclodextrin.diclofenac-Na: | | |
| C | 46.11% | 45.73% |
| H | 5.68% | 6.36% |
| N | 0.87% | 1.15% |
| Cl | 4.39% | 4.35% |
| Na | 1.42% | 1.43% |
| γ-cyclodextrin.diclofenac-K: | | |
| C | 45.61% | 45.75% |
| H | 5.58% | 5.53% |
| N | 0.86% | 0.82% |
| Cl | 4.35% | 4.41% |
| K | 2.40% | 2.36% |

2. Thermogravimetric analysis (TG):

The samples are stored for 9 days at 52% relative humidity and room temperature. The measurement is made using the Perkin-Elmer TGS 2 thermogravimetric system.

| Substance | Temperature | Mass loss |
|---|---|---|
| diclofenac-Na | up to 100° C. | 20.7% |
| | up to 200° C. | 20.8% |
| | up to 280° C. | 22.2% |
| diclofenac-K | up to 100° C. | <0.1% |
| | up to 200° C. | <0.1% |
| | up to 280° C. | 0.2% |
| γ-cyclodextrin | up to 100° C. | 15.7% |
| | up to 200° C. | 17.3% |
| | up to 280° C. | 19.3% |
| γ-cyclodextrin.diclofenac-Na | up to 100° C. | 12.3% |
| | up to 200° C. | 13.7% |
| | up to 200° C. | 65.3% |
| γ-cyclodextrin.diclofenac-K | up to 100° C. | 4.6% |
| | up to 200° C. | 6.5% |
| | up to 200° C. | 10.5% |

3. Differential scanning calorimetry (DSC):

The samples are stored for 9 days at 52% relative humidity and room temperature. The measurement is made using a Perkin-Elmer thermoanalyser (Series 7).

| Substance | Peak [°C.] | ΔH [J/g] |
|---|---|---|
| diclofenac-Na | 56.6 | 40 |
| | 114.2 | 79 |
| | 130.3 | 6 |
| diclofenac-K | 297.9 | |
| γ-cyclodextrin | 100.3 | 8 |
| | 130.1 | 16 |
| γ-cyclodextrin.diclofenac-Na | 127.2 | 37 |
| | 180.6 | 17 |
| γ-cyclodextrin.diclofenac-K | 78.1 | 3 |
| | 216.3 | 22 |

4. X-Ray powder analysis

The measurement is made using a Guinier camera (FR 552, Enraf-Nonius) in gamma-ray geometry. The diagrams are recorded by copper-$K\alpha_1$-radiation ($\lambda = 1.54060 \times 10^{-10}$ m) on X-ray film. A diagram of quartz recorded on the same film is used for calibrating the camera radius.

The following Table lists the lattice distances (d-values and the relative intensities of the most important reflexes with d-values>$3.5 \cdot 10^{-10}$ m):

| d-values [$10^{-10}$ m] | Intensities |
|---|---|
| γ-cyclodextrin.diclofenac-Na | |
| 15.40 | average |
| 14.60 | strong |
| 8.40 | weak |
| 7.70 | average |
| 7.30 | weak |
| 6.40 | average |
| 6.10 | very weak |
| 5.51 | very strong |
| 4.86 | weak |
| 4.60 | very weak |
| 4.39 | very weak |
| 4.06 | average |
| 3.65 | weak |
| γ-cyclodextrin.diclofenac-K | |
| 15.10 | strong |
| 14.60 | average |
| 13.40 | strong |
| 8.40 | weak |
| 8.20 | very weak |
| 7.70 | average |
| 7.50 | average |
| 7.30 | very strong |
| 6.70 | weak |
| 6.50 | weak |
| 5.95 | very weak |
| 5.71 | very weak |
| 5.51 | very weak |
| 5.23 | average |
| 4.96 | average |
| 4.79 | very weak |
| 4.74 | very weak |
| 4.61 | very weak |
| 4.45 | weak |
| 4.41 | weak |
| 4.37 | average |
| 4.26 | average |
| 4.20 | weak |
| 4.12 | weak |
| 4.04 | average |
| 3.91 | very weak |
| 3.84 | very weak |
| 3.78 | very weak |
| 3.73 | weak |
| 3.67 | very weak |
| 3.64 | weak |
| 3.50 | very weak |

5. IR Spectroscopy:

The diclofenac sodium-γ-cyclodextrin 1:1 mixture is prepared by dry mixing the salt of diclofenac with γ-cyclodextrin. The measurement is made with a FTIR spectrophotometer IFS 48 supplied by Bruker. The wave numbers are given in $cm^{-1}$. The shape of the bands is described in more detail by qualifying affixed: vst=very strong; st=strong; av=average; wk=weak; b=broad.

| Diclofenac-Na | γ-Cyclodextrin | Diclofenac-Na+ γ-cyclodextrin 1:1 mixture | Diclofenac-Na. γ-cyclodextrin inclusion cmpd. |
|---|---|---|---|
|  | 1639 av, b | 1636 wk | 1634 wk |
| 1576 vst |  | 1578 av | 1578 av |
| 1556 vst |  | 1556 av | 1560 wk |
| 1508 vst |  | 1508 av | 1504 av |
| 1391 vst | 1369 av | 1389 av, b | 1377 av, b |
| 953 wk | 941 av | 943 av | 941 av |
| 868 av |  |  |  |
| 839 av | 854 wk | 843 wk | 860 wk, b |
| 716 av | 708 av | 714 av | 706 av |
| 685 av |  |  |  |

| Diclofenac-K | γ-Cyclodextrin | Diclofenac-K+ γ-cyclodextrin 1:1-mixture | Diclofenac-K. γ-cyclodextrin inclusion cpd. |
|---|---|---|---|
| 1504 st |  | 1504 st | 1506 st |
| 1468 st |  | 1468 st | 1472 av |
| 1452 st | 1414 av | 452 st | 1456 st |
| 1304 st | 1369 av | 306 w | 1315 av |
| 1153 w | 1157 st | 1146 w | 1144 w |
| 947 av | 941 av | 951 w | 939 w |
| 766 av | 758 v | 768 av | 775 w |
| 746 av |  | 746 av | 744 w |
| 717 w | 708 av | 717 w | 702 w |

6. Circular dichroism:

The spectra are recorded with a Jasko 710 dichrograph. The molar ellipticity for γ-cyclodextrin-diclofenac sodium $[\Theta]_c = 102 \pm 6°$ $M^{-1}$ $cm^{-1}$ and for γ-cyclodextrin-diclofenac-potassium $[\Theta]_c = 84 \pm 6°$ $M^{-1}$ $cm^{-1}$ (at 272 nm in 69 nM phosphate buffer solution, pH 7,4).

Excipients customarily used for the preparation of solid dosage forms are preferably excipients for tabletting, especially those that are suitable for direct compression, e.g. powder binders such as starch, e.g. potato starch, wheat starch and corn starch, microcrystalline cellulose, e.g. products that are commercially available under the registered trademark Avicel®, Filtrak®, Heweten® or Pharmacel®, highly dispersed silica, e.g. Aerosil®, mannitol, lactose, and also polyethylene glycol, preferably having a molecular mass of 4000 to 6000, crosslinked polyvinyl pyrrolidone (Polyplasdone® XL or Kollidon® L), crosslinked carboxymethyl cellulose (Acdisol® CMC-XL), carboxymethyl cellulose [Nymcel® (Nyma)], carboxymethyl starch [Explotab® (Mendell) or Primojel® (Scholtens)], dicalcium phosphate, e.g. Eracompress®, or talcum. The addition of minor mounts of glidants such as magnesium stearate is also useful.

Further excipients are siliconised talcum, aluminium stearate, stearic acid, palmitic acid, skimmed milk powder, stearyl, cetyl and myristyl alcohol, Lanette® 0, paraffin or hydrogenated fats. With respect to tabletting, attention is drawn to the comprehensive technical literature on the subject.

The compression to tablet cores can be carried out in a conventional tabletting machine, e.g.. in an EK-0 Korsch eccentric tabletting machine, preferably at a compression greater than 10 kN. The tablet cores may vary in shape and be, for example, circular, oval, oblong, cylindrical and the like, and may also vary in size depending on the concentration of therapeutic chug. They may furthermore be transparent, colourless, coloured and also marked so as to impart to these products an individual appearance and to make them instantly recognisable. The use of dyes can serve to enhance the appearance as well as to identify the compositions. Dyes suitable for use in pharmacy typically include carotinolds, iron oxides or chlorophyll.

The compressed tablet cores formed by direct tabletting can, if desired, be further processed in per se known manner to another solid dosage form, typically to dragées that are provided with an additional coating, e.g. a sugar, shellac, coloured or film coating. Attention is dram to the numerous known methods employed in the art of tabletting, e.g. spray coating in a fluidised bed, e.g. by the known methods using apparatus available from Aeromatic, Glatt, Wurster or Hüttlin, in a spray vat by the Accela Coata method, or to the submerged-coil coating method. The excipients commonly used in confectioning are employed in such methods.

A further object of this invention is the per se known process for the preparation of the inclusion compound of diclofenac, or a pharmaceutically acceptable salt thereof, in γ-cyclodextrin, which comprises reacting diclofenac, or a pharmaceutically acceptable salt thereof, with γ-cyclodextrin in the presence of water.

This process can be carded out using a number of process variants, typically by a) adding water to a mixture of diclofenac, or a pharmaceutically acceptable salt thereof, with γ-cyclodextrin, and stirring the mixture at elevated temperature, preferably in the range from 50°–60° C., and then, without or after cooling, precipitating or crystallising the resultant inclusion compound, or b) adding water to a mixture of diclofenac, or the salt thereof, and γ-cyclodextrin, and subsequently precipitating or crystallising the rsultant inclusion compound, or c) in any order, adding a minor amount of water first to diclofenac or to the salt thereof or γ-cyclodextrin, kneading or agitating the moistened paste and adding thereto the second component of the inclusion compound, or d) preparing an aqueous suspension of diclofenac, or the salt thereof, and γ-cyclodextrin, converting said suspension into a solution by adjusting the pH to the alkaline range, typically by adding a base such as a solution of ammonia or dilute aqueous sodium or potassium hydroxide solution, and thereafter neutralising this solution with an acid or a buffer solution, conveniently by adding dilute aqueous sulfuric acid or hydrochloric acid or acetic acid, and subsequently precipitating or crystallising the resultant inclusion compound, and then, after carrying out any one of process variants a) to d), purifying or isolating the resultant inclusion compound.

The inclusion compound can be purified or isolated by washing the precipitated or crystallised product with a minor mount of an organic solvent, e.g. ethanol or acetone, in which in particular diclofenac or the salt thereof dissolves more readily than the inclusion compound.

γ-Cyclodextrin is also known as cyclooctaamylose, q.v. Merck Index, Eleventh Edition, No. 2724. This excipient is a commercially available (Wacker Chemie) degradation product of starch and consists of 8 glucose units that are linked to one another in cyclic conformation through glycosidic bonds.

Specification:

| | |
|---|---|
| water content when filled: | 6.6% |
| D.E. (dextrose equivalent): | 0.05 |
| ignition residue: | <0.05% |
| minimum conc. of γ-cyclodextrin: | >99.5% |
| conc. of α-cyclodextrin: | <0.1% |
| conc. o β-cyclodextrin: | <0.1% |
| conc. of linear oligosaccharides: | <0.1% (max.) |
| turbidity of a 10% solution at 420 nm: (1 cm layer thickness): | 0.16 |
| manufacturer: | Wacker Chemie (DE) |

EXAMPLE 1

1.1 preparation of the inclusion compound:

12.31 g (38.7 mmol) of diclofenac sodium and 50.19 g (38.7 retool) of γ-cyclodextrin are dissolved in c. 150 ml of water at 75° C. The solution is filtered and slowly allowed to cool to room temperature, whereupon colourless needle-shaped crystals precipitate. After standing for 3 days in a refrigerator, the crystals are isolated by centrifugation at 10° C. and 400 rpm. The crystalline residue is washed with a small mount of ice-water and dried to constant weight at 40° C. in a drying oven under vacuum (c. 200 mbar). Yield: 39.30 g (62.9% of theory) based on the anhydrous substance (water content: 7.31% after Karl-Fischer titration).

1.2 Direct tabletting:

| | |
|---|---|
| γ-cyclodextrin.diclofenac sodium | 100 mg (69.9%) |
| Avicel ® PH 102 | 35 mg (24.5%) |
| polyvinyl pyrrolidone PXL | 6 mg (4.2%) |
| Aerosil ® 200 | 1 mg (0.7%) |
| magnesium stearate | 1 mg (0.7%) |

γ-Cyclodextrin-diclofenac-sodium is mixed with 0.5–1, 0% magnesium stearate and pressed to talbets of 250 mg wight at a pressure of about 130 MN/m² in a Korsch DSKi 118 eccentric tabletting machine equipped with compacting pressure registration and a plain punch of 9 mm diameter. The tablets obtained have a height of 3.0±0,01 mm and a breaking resistance of 120±32N measured in a Schleuniger 6 D fractographer (Schleuniger Prodrutronic AG, CH-4501 Solothrun).

EXAMPLE 2

| | |
|---|---|
| γ-cyclodextrin.diclofenac-sodium | 250.0 mg (69.9%) |
| Avicel ® PH 102 | 87.5 mg (24.5%) |
| polyvinyl pyrrolidone PXL | 15.0 mg (4.2%) |
| Aerosil ® 200 | 2.5 mg (0.7%) |
| magnesium stearate | 2.5 mg (0.7%) |

The inclusion compound and the excipients are mixed in a Turbula® T2C mixer for 15 min.. The magnesium stearate is added to this mixture and mixing is continued for 3 min.. Then 358 mg of the formulation mixture are fried into each of the matrices and processed to tablets at about 80 MN/m² in a Korsch DSKi 118 eccentric tabletting machine with compacting pressure registration und a plain punch of 6 mm diameter. The tablets obtained have a height of 4.2±0.04 mm and a breaking resistance of 160±23N measured in a Schleuniger 6 D fractographer.

EXAMPLE 3

| | |
|---|---|
| γ-cyclodextrin.diclofenac-sodium | 250.0 mg (67.8%) |
| corn starch | 49.6 mg (5.2%) |
| Na-carboxymethyl starch | 19.5 mg (6.0%) |
| Aerosil ® 200 | 4.5 mg (1.4%) |
| magnesium stearate | 2.1 mg (0.6%) |

The inclusion compound and the excipients are mixed in a Turbula® T2C mixer for 15 min.. The magnesium stearate is added to this mixture and mixing is continued for 3 min.. Then 326 mg of the formulation mixture are filled into each of the matrices and processed to tablets at about 180 MN/m² in a Korsch DSKi 118 eccentric tabletting machine with compacting pressure registration und a plain punch of 9 mm diameter. The tablets obtained have a height of 4.0±0.05 mm and a breaking resistance of 110±21N measured in a Schleuniger 6 D fractographer.

EXAMPLE 4

| | |
|---|---|
| diclofenac-Na | 50,0 mg (15,4%) |
| γ-cyclodextrin | 200, 0 mg (61, 4%) |
| corn starch | 49, 6 mg (15, 2%) |
| Na-carboxymethyl starch | 19, 5 mg (6, 0%) |
| Aerosil ® 200 | 4, 5 mg (1, 4%) |
| magnesium stearate | 2, 1 mg (0, 6%) |

Diclofenac-Na, γ-cyclodextrin and Na-carboxymethyl starch 32.4 g corn starch und 2,2 g AEROSIL are admixed for 15 minutes in a mixer "Kitchen Aid" (Hoball, Regensdorf CH) at speed level 1. 100 g water is added in portions, and the mixture obtained is mixed for further 15 minutes. The mixture is meshed through a screen and dried until a moisture content of about 10% (relative to the mass of the dry composition) is reached. The powder is admixed for 15 minutes in the TURBULA mixer with the remaining amounts of corn starch and AEROSIL. The magnesium stearate is then added and the mixture is further mixed for another 3 minutes. Then 326 mg of the formulation mixture are filled into each of the matrices and processed to tablets at about 150 MN/m² in a Korsch DSKi 118 eccentric tabletting machine with compacting pressure registration und a plain punch of 9 mm diameter. The tablets obtained have a height of 4.02±0.02 mm and a breaking resistance of 195±22N.

EXAMPLE 5

In a manner analogous to Example 1 tablets are manufactured characterized by a content of 261 mg γ-cyclodextrin-diclofenac-potassium. The tablets obtained have a height of 3.4±0,1 mm and a breaking resistance of 180±26 N.

EXAMPLE 6

In a manner analogous to Example 3 tablets are manufactured characterized by a content of 261 mg γ-cyclodextrin-diclofenac-potassium. The tablets obtained have a height of 4.5±0,1 mm and a breaking resistance of 190±22 N.

What is claimed is:

1. A process for the preparation of compressed tablets containing diclofenac or a pharmaceutically acceptable salt thereof, which comprises preparing an inclusion compound consisting of γ-cyclodextrin and a therapeutic agent selected from the group consisting of diclofenac and a pharmaceutically acceptable salt thereof, and compressing said inclusion compound directly into compressed tablets, with the addition of pharmaceutically-acceptable excipients.

2. A process according to claim 1, wherein the therapeutic agent is diclofenac sodium.

3. A process according to claim 1, wherein the pharmaceutically-acceptable excipients are binders and glidants.

4. A process for the preparation of dragées containing diclofenac or a pharmaceutically acceptable salt thereof, which comprises preparing compressed tablets according to the process of claim 1, and coating the compressed tablets with a pharmaceutically-acceptable coating to form dragées.

5. A process for the preparation of an inclusion compound comprising γ-cyclodextrin and a therapeutic agent selected from the group consisting of diclofenac and a pharmaceutically acceptable salt thereof, which comprises reacting the therapeutic agent with γ-cyclodextrin in the presence of water, wherein the step of reacting the therapeutic agent with γ-cyclodextrin in the presence of water is accomplished by preparing an aqueous suspension of the therapeutic agent and γ-cyclodextrin, converting said suspension into a solution by adjusting the pH to the alkaline range, neutralizing this solution with an acid or a buffer solution, and precipitating or crystallizing the resultant inclusion compound, and purifying or isolating the resultant inclusion compound.

* * * * *